United States Patent
Kim et al.

(10) Patent No.: US 7,466,853 B2
(45) Date of Patent: Dec. 16, 2008

(54) METHOD AND APPARATUS FOR DETECTING DEFECTS ON A WAFER

(75) Inventors: Deok-Yong Kim, Gyeonggi-do (KR); Byoung-Ho Lee, Gyeonggi-do (KR)

(73) Assignee: Samsung Electronics Co., Inc., Suwon-si, Gyeonggi-do (KR)

( * ) Notice: Subject to any disclaimer, the term of this patent is extended or adjusted under 35 U.S.C. 154(b) by 822 days.

(21) Appl. No.: 10/749,670

(22) Filed: Dec. 30, 2003

(65) Prior Publication Data

US 2004/0150813 A1   Aug. 5, 2004

(30) Foreign Application Priority Data

Jan. 2, 2003   (KR)   ............ 10-2003-0000102

(51) Int. Cl.
*G06K 9/00*   (2006.01)

(52) U.S. Cl. ............................ 382/145; 382/273

(58) Field of Classification Search ......... 382/144–150, 382/141, 172; 389/145, 273
See application file for complete search history.

(56) References Cited

U.S. PATENT DOCUMENTS

| | | | | |
|---|---|---|---|---|
| 2,349,012 | A * | 5/1944 | Spaeth | 315/244 |
| 6,087,673 | A * | 7/2000 | Shishido et al. | 250/559.45 |
| 6,091,846 | A * | 7/2000 | Lin et al. | 382/145 |
| 6,175,417 | B1 * | 1/2001 | Do et al. | 356/392 |
| 6,498,867 | B1 * | 12/2002 | Potucek et al. | 382/274 |
| 6,980,686 | B2 * | 12/2005 | Kuwabara | 382/145 |
| 7,116,816 | B2 * | 10/2006 | Tanaka et al. | 382/149 |
| 7,142,708 | B2 * | 11/2006 | Sakai et al. | 382/149 |
| 7,171,038 | B2 * | 1/2007 | Adler et al. | 382/149 |

(Continued)

FOREIGN PATENT DOCUMENTS

JP   2001-133418   5/2001

OTHER PUBLICATIONS

Nagaswami et al., Application of Segmented Auto Threshold (SAT) for 0.5um and 0.35um Logic Interconnect Layers, Sep. 10-12, 1997, Advanced Semiconductor Manufacturing Conference and Workshop, 1997, IEEE/SEMI, pp. 126-135.*

(Continued)

*Primary Examiner*—Matthew C Bella
*Assistant Examiner*—Dennis Rosario
(74) *Attorney, Agent, or Firm*—Marger Johnson & McCollom, P.C.

(57) ABSTRACT

A light is irradiated on a wafer including a plurality of pixels. Image information corresponding to each pixel is measured by sensing the light reflected by the wafer surface. A raw datum is calculated by subtracting the image information of a corresponding pixel from the image information of a target pixel. The target pixel is a subject pixel for detecting a defect. The corresponding pixel is a pixel located in a first device unit and corresponds to the target pixel. The first device unit is located adjacent to a second device unit that includes the target pixel. The threshold region is preset to have at least one pair of upper and lower limits. The target pixel is marked as a defective pixel when the raw datum thereof is included in the threshold region. Accordingly, the killer defect can be detected separate from the non-killer defects that are usually detected together with the killer defects.

27 Claims, 10 Drawing Sheets

U.S. PATENT DOCUMENTS 7,269,280 B2 * 9/2007 Hiroi et al. .................. 382/149
7,274,813 B2 * 9/2007 Maeda et al. ............... 382/141
2003/0007677 A1 * 1/2003 Hiroi et al. .................. 382/149

OTHER PUBLICATIONS

English language abstract of Japanese Publication. No. 2001-133418.

* cited by examiner

METHOD AND APPARATUS FOR DETECTING DEFECTS ON A WAFER

CROSS-REFERENCE OF RELATED APPLICATIONS

This application claims priority upon Korean Patent Application No. 2003-00102 filed on Jan. 2, 2003, the contents of which are herein incorporated by reference in their entirety.

BACKGROUND OF THE INVENTION

1. Field of the Invention

The present invention relates to a method and an apparatus for detecting a defect on a wafer.

2. Description of the Related Art

In general, fine patterns of semiconductor integrated circuits formed on a wafer are inspected for detecting pattern defects after performing a semiconductor fabrication process step or a series of semiconductor fabrication process steps. As semiconductor devices become more highly integrated and a diameter of the wafer becomes larger, the inspection process for detecting defects on the wafer is more frequently carried out. Therefore, overall manufacturing time for manufacturing the semiconductor device has been significantly increased, thereby raising the manufacturing cost of the semiconductor devices.

Conventionally, an individual gray level corresponding to each of pixels on the wafer is measured, and the gray level of a target pixel and the gray levels of neighboring pixels adjacent to the target pixel are compared with each other. Then, the gray level difference is calculated. The inspection process detects defects of the wafer by using the gray level difference. The inspection process is classified into an array mode and a random mode. While the array mode compares respective cells in a chip on the wafer for detecting defects, the random mode compares respective die for detecting defects. The array mode is usually used in semiconductor memory device fabrication process, and the random mode is usually used in logic device fabrication process. Hereinafter, the inspection process for detecting defects will be explained for the array mode.

In general, the widespread array mode inspection process uses a threshold value for detecting defects on the wafer. The gray level difference between the target pixel and the neighboring pixels adjacent to the target pixel is compared with a preset threshold value. When the gray level difference is greater than the preset threshold value, the target pixel is indicated as a defective pixel. On the contrary, when the gray level difference is less than the threshold value, the target pixel is indicated as a non-defective pixel.

Figure 1:
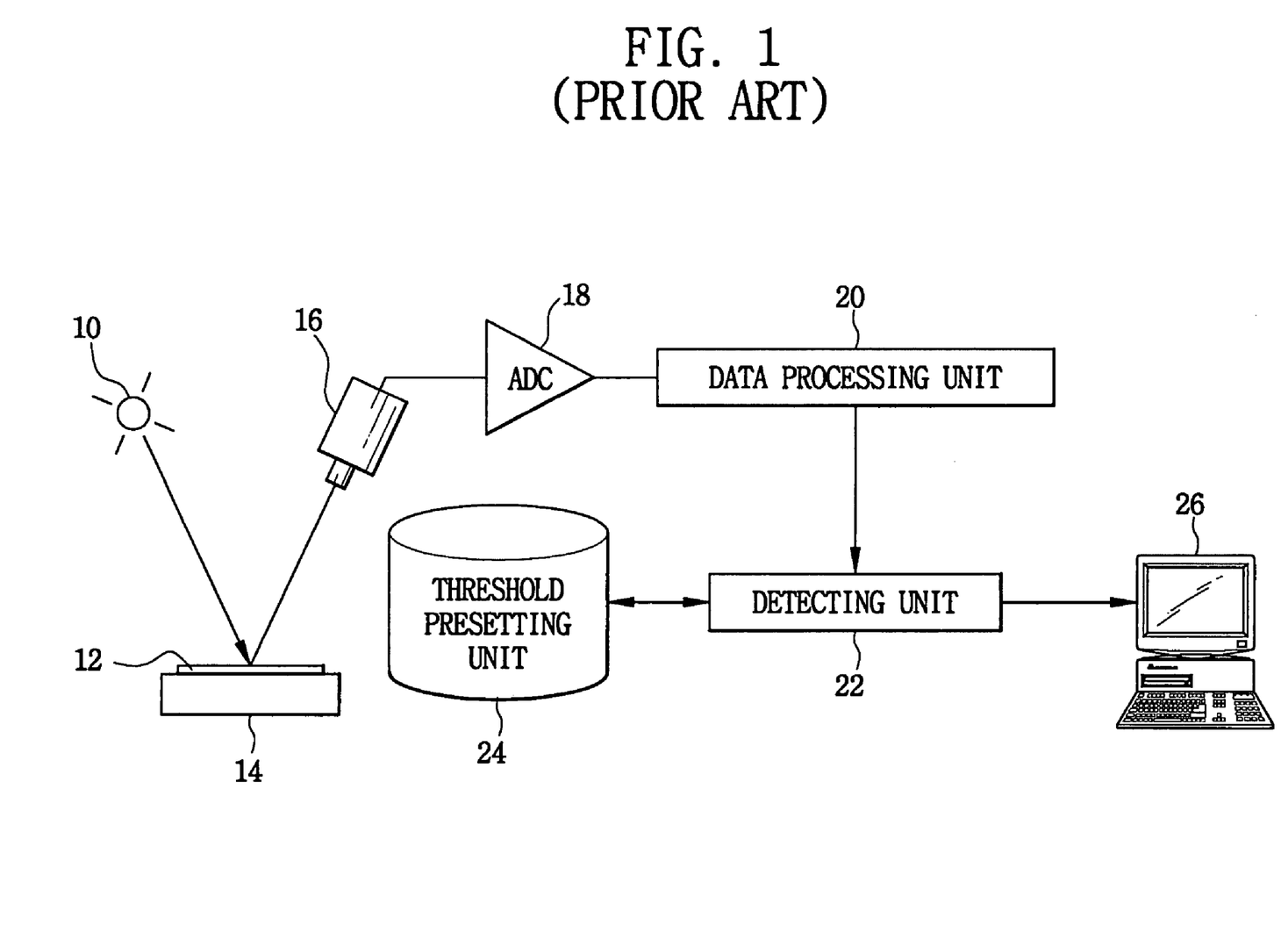
FIG. 1 is a schematic diagram showing a conventional inspector.

FIG. 1 is a schematic diagram showing a conventional inspector. Referring to FIG. 1, a wafer 12 on which predetermined process steps have been carried out is loaded on a support 14 for detecting process defects on the wafer. The wafer 12 is loaded/unloaded to/from the support 14 by the conventional loading mechanism such as a robot arm. A light source 10 irradiates a light to each cell on a surface of the wafer 12. Then, the light is reflected from the surface of the wafer 12. The reflected light is detected by an image detecting means 16 including a photo-sensor, and as a result, an analog image signal is generated. The analog image signal is converted into a digital image signal by an analog-to-digital converter (ADC). Thus, gray levels corresponding to respective pixels comprising each cell on the wafer are formed. The gray level is processed with 8-bit digital signal, so that each pixel of the cell may have 256 kinds of gray levels. Therefore, gray levels corresponding to every pixel form the digital image corresponding to a cell on the wafer, and all the digital images corresponding to every cell forms an image map corresponding to one sheet of the wafer. Then, a data process unit 20 generates a raw datum. The raw datum is a gray level difference between the gray level of the target pixel and the gray level of the neighboring pixel adjacent to the target pixel. On the other hand, a threshold presetting unit 24 presets a threshold value, which is used for judging whether a defect is formed on the wafer. The raw datum is calculated into an absolute value, and is compared with the threshold value. The defect on the wafer is detected using a detecting unit 22. The detecting unit 22 includes a central process unit (CPU) and a co-processor, and detects the defect on the wafer by using a main program and a sub-program. The result of the detecting unit 22 is displayed on a monitor of the operating terminal 26.

Figure 2:
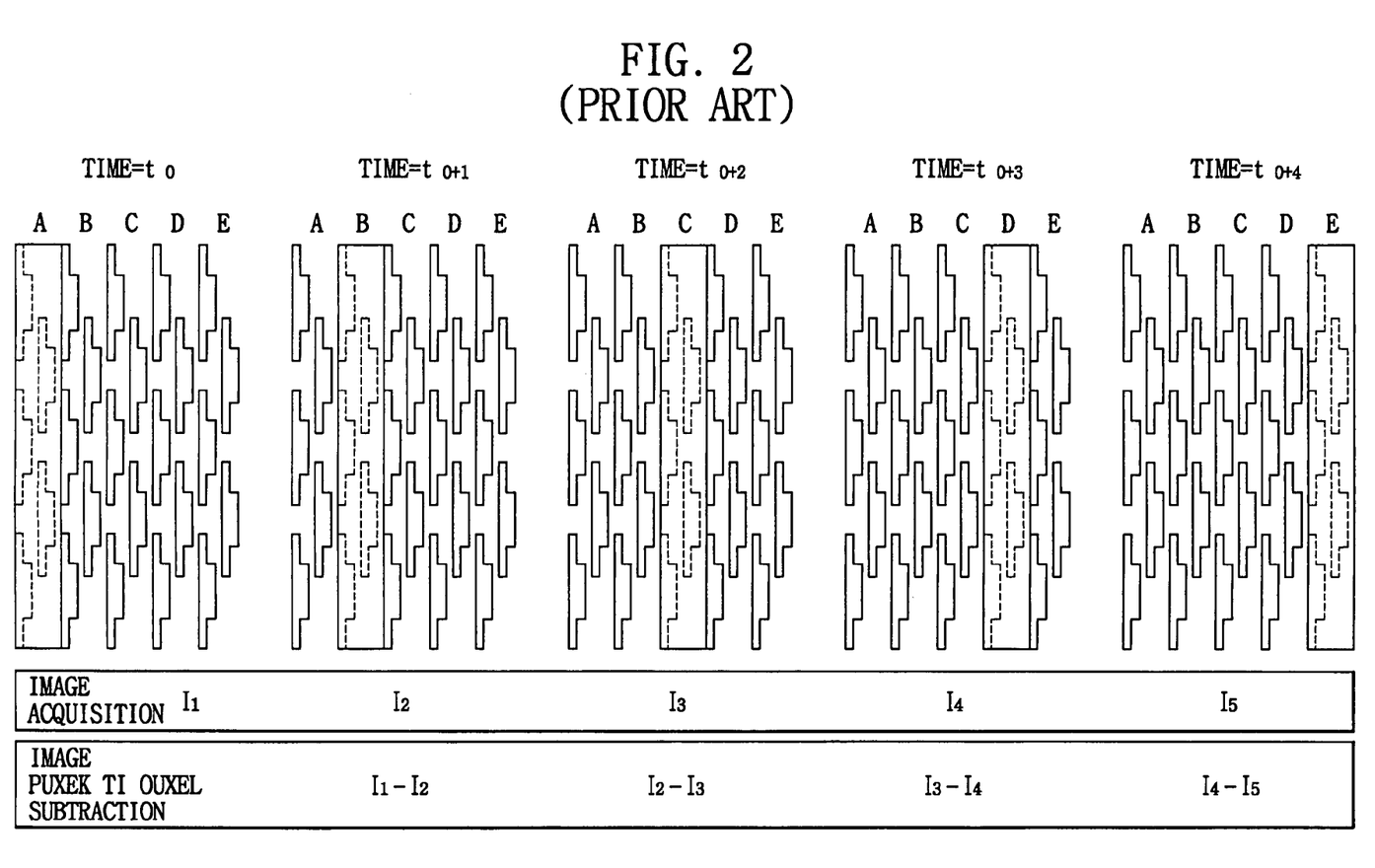
FIG. 2 is a diagram explaining the generation of the raw datum by the data process unit shown in FIG. 1.

FIG. 2 is a diagram explaining the generation of the raw datum by the data process unit shown in FIG. 1.

Referring to FIG. 2, a light is irradiated on a first cell A that is an arbitrary cell on the wafer at an arbitrary time $t_0$. A first image $I_1$ corresponding to the first cell A is obtained. Next, a light is irradiated on a second cell B adjacent to the first cell at a time $t_{0+1}$ after a lapse of unit time from the time $t_0$, and a second image $I_2$ corresponding to the second cell B is obtained. A third image corresponding to the third cell, a fourth image corresponding to the fourth cell, and a fifth image corresponding to the fifth cell are sequentially obtained in the same manner. Thus, the image map corresponding to an entire surface of the wafer is obtained. The size of the cell is determined such that the same pattern is repeated for every image obtaining step. Each of the images is represented as the gray level of the pixels comprising the respective cells on the wafer, and the gray level is binary digital data. Therefore, an image difference $I_1-I_2$ between the first and second images is the binary digital datum.

Figure 3:
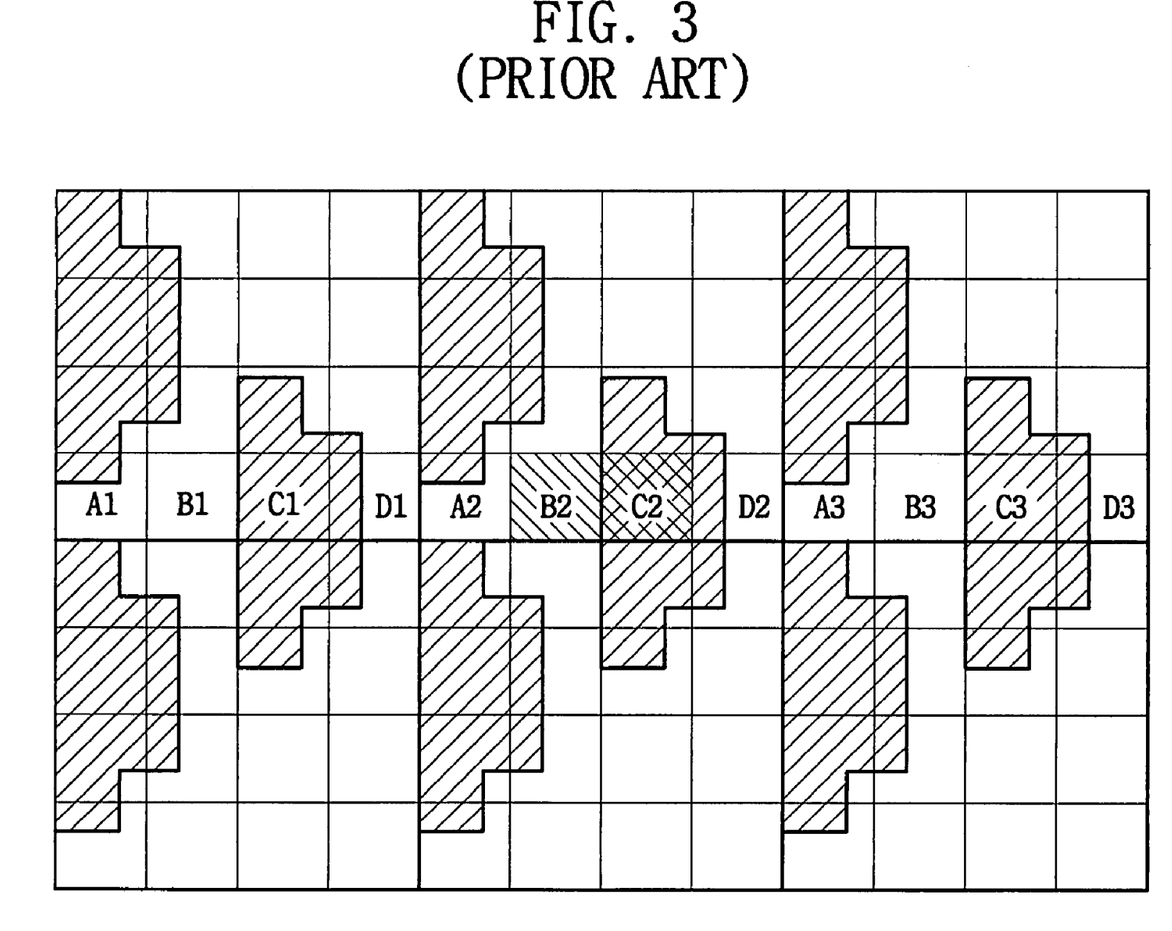
FIG. 3 is a diagram explaining a process for detecting a defect on the wafer by using the detecting unit shown in FIG. 1.

FIG. 3 is a diagram explaining a process for detecting the defects on the wafer by using the detecting unit shown in FIG. 1. FIG. 3 shows arbitrary 3 cells neighboring each other on the wafer for simplicity. The same alphabetic letter indicates a pixel located on the same position on different cells, and the same numeric letter indicates an identical cell.

An experiment shows that the gray levels of each pixel B1, B2, and B3 of FIG. 3 are 50, 100, 50, respectively, and the gray levels of each pixel C1, C2, and C3 of FIG. 3 are 60, 30, 60, respectively. That is, the B2 pixel is more luminescent than the B1 and B3 pixels, and the C2 pixel is less luminescent than the C1 and C3 pixels. The raw datum of the B2 pixel is the gray level difference between the B2 pixel and the adjacent pixels B1 and B3. That is, the raw datum of the B2 pixel is calculated as the gray level difference of (gray level of B2 pixel–gray level of B1 pixel) and (gray level of B2 pixel–gray level of B3 pixel). In the same way, the raw datum of the C2 pixel is calculated as the gray level difference of (gray level of C2–gray level of C1) and (gray level of C2–gray level of C3). According to the present experiment, the raw datum of the B2 pixel is 50, and the raw datum of the C2 pixel is –30. The negative raw datum is converted into the same positive value by converting into an absolute value. When the threshold value is 40, the B2 pixel is checked as a defective pixel and the C2 pixel is checked as a non-defective pixel.

Figure 4:
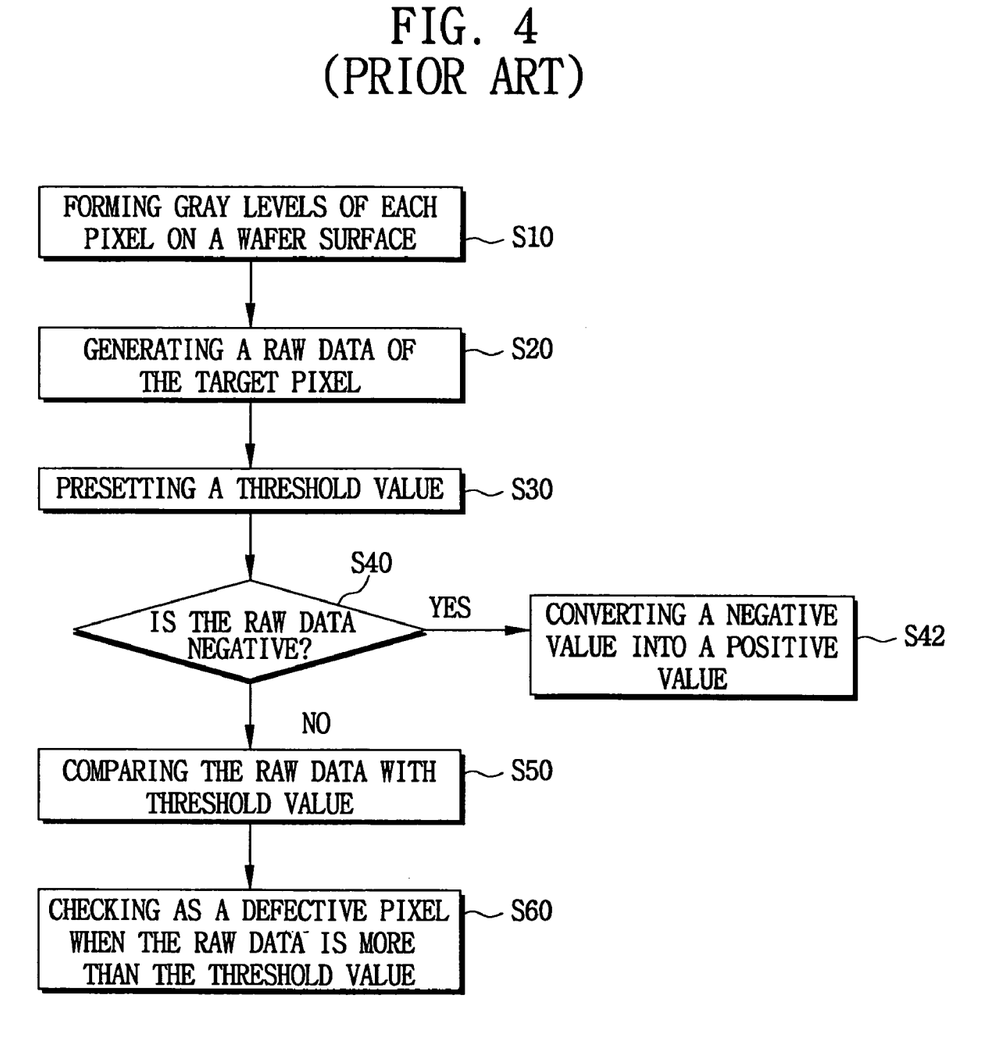
FIG. 4 is a flow chart illustrating a conventional method of detecting a defect on the wafer

FIG. 4 is a flow chart illustrating a conventional method of detecting a defect on the wafer.

Referring to FIG. 4, a light is irradiated on a surface of the wafer on which a thin film is deposited, and in step S10, gray levels of each pixel on the wafer are formed. In next step S20, the raw datum that is the gray level difference between the target pixel and the neighboring pixel is generated, and in step S30, the threshold value that is a criterion for judging defectiveness after compared with the raw datum is preset. In step S40, the raw datum is checked whether or not the value is negative. When the raw datum has a negative value, the raw datum is converted into the positive value by using the absolute value of the negative raw datum in step S42. In subsequent step S50, the raw datum is compared with the threshold value, and when the raw datum is more than the threshold value, the target pixel is checked as a defective pixel in step S60.

However, the conventional detecting method has the following problems:

First, a killer defect, meaning a serious defect, and a non-killer defect, meaning a non-serious defect, are simultaneously detected because all of the target pixels of which the absolute value of the raw datum is more than the threshold are checked as a defective pixel. Therefore, the killer defect and the non-killer defect are not easily separated from each other.

A process of after-develop inspection (ADI) is carried out on a surface of the wafer on which 0.09 mm design rule is applied for detecting a micro-bridge that is a killer defect found on a gate of a non-versatile memory (hereinafter, referred to as NVM). According to the ADI data measured by the STEALTH (trade name, a detecting apparatus made by KLA-Tencor Co. Ltd. U.S.A.), about 50% of the detected defects were sub-defect that is a common defect found under the layer, and about 40% of the detected defects were a non-visual defect such as the false defect that is not visible through the scanning-electron microscope (SEM) and caused by the interference of the incident light or the operating error of detecting apparatus. That is, about 90% of the detected defects were non-killer defects.

Figure 5:
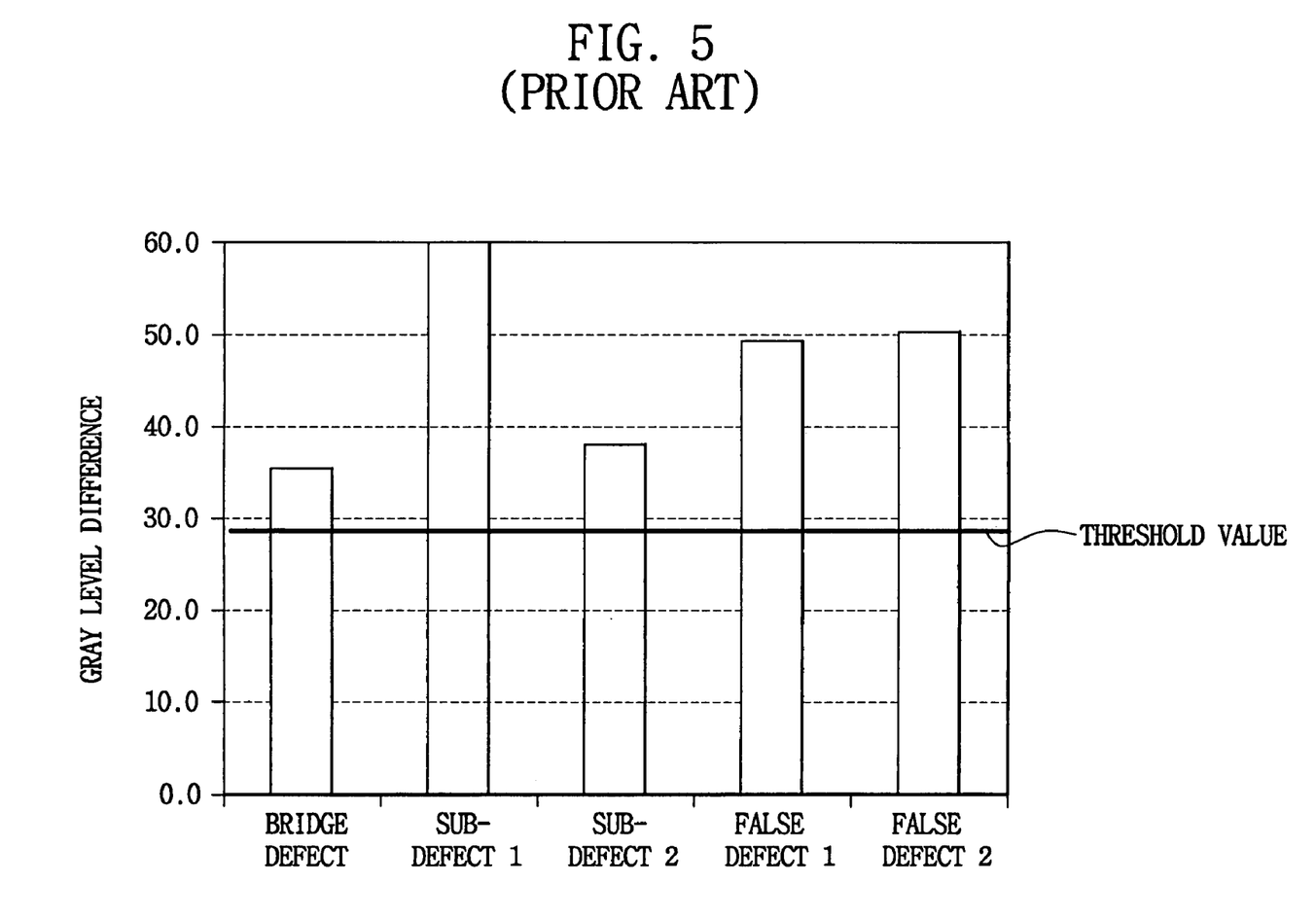
FIG. 5 is a diagram showing the gray level difference with respect to the defect type detected on the NVM by using the conventional inspector shown in FIG. 1.

FIG. 5 is a diagram showing the gray level difference with respect to the defect type detected on the NVM. The horizontal axis of the diagram indicates the defect type, and the vertical axis of the diagram indicates the gray level difference.

FIG. 5 confirms that the gray level differences of the sub-defect and the false defect are greater than the gray level difference of the bridge defect that is the killer defect generated during the NVM fabricating process. Therefore, when the threshold value is exemplarily preset as about 30 for detecting the bridge defect, the sub-defect and the false defect are also detected with the bridge defect. Therefore, the bridge defect is not separated from the sub-defect and the false defect.

Second, when the negative raw datum is converted into a positive value by using an absolute value of the negative raw datum, an originally positive raw datum is not distinguished from the converted positive raw datum. Therefore, the defect corresponding to the originally positive raw datum and the defect corresponding to the converted positive raw datum are simultaneously detected, so that the detected defect cannot be verified.

An inspection process is carried out on a surface of the wafer on which 0.123 mm design rule is applied after patterning process for forming a S-poly (storage node with polysilicon), and the respective gray levels of the detected defects are measured. The inspection discloses not only, for example, a striation defect which is a common defect of the S-poly patterning process, and the false defect, but also a leaning defect that is a killer defect of the S-poly patterning process. The false defect is not visible through the scanning-electron microscope (SEM), and it is caused by the interference of the incident light or the operating error of detecting apparatus.

Figure 6:
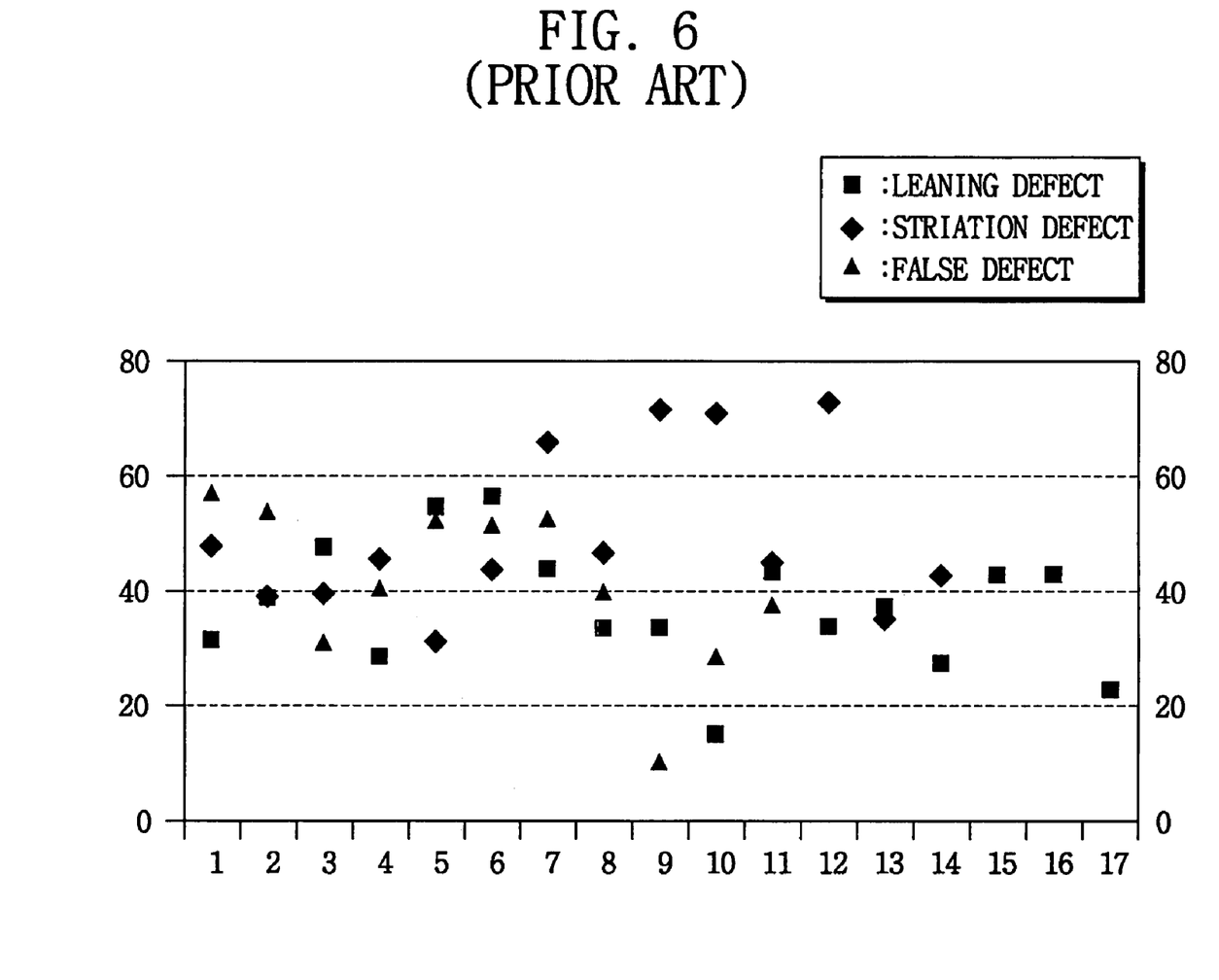
FIG. 6 is a diagram showing the gray level difference with respect to the defect type during the S-poly patterning process by using the conventional inspector shown in FIG. 1.

FIG. 6 is a diagram showing the gray level difference with respect to the defect type during the S-poly patterning process. The horizontal axis of the diagram indicates an arbitrary position on the surface of the wafer, and the vertical axis of the diagram indicates the gray level difference.

Referring to FIG. 6, when the gray level difference is in a range between about 20 and about 60, not only the leaning defect but also the striation defect is most frequently detected. Therefore, when the threshold value is preset as one of the range between about 20 and about 60, the leaning defect and the striation defect are always detected together.

The false defect is more frequently detected because the design rule is becoming smaller and smaller. Therefore, inspection time for detecting the killer defect is getting longer, thereby reducing the productivity of fabricating semiconductor devices.

SUMMARY OF THE INVENTION

Accordingly, the present invention is directed to a method and an apparatus for preventing various types of defects from being detected together by using a threshold region including a pair of upper and lower limits that are compared with the raw datum of a target pixel.

According to one embodiment of the present invention, a method of detecting defects on a substrate includes irradiating a light on a substrate, measuring image information on each pixel on the substrate, calculating a raw datum of a target pixel, presetting a threshold region, comparing the threshold region with the raw datum, and g) checking the target pixel as a defective pixel. Preferably, a plurality of device units are formed on a surface of the substrate, and each of the device units includes a plurality of pixels. The image information of a pixel is formed by sensing the light reflected by a surface of the substrate. The raw datum of the target pixel is formed by subtracting the image information of a corresponding pixel from the image information of the target pixel. The target pixel is a subject pixel for detecting defects. The corresponding pixel is a pixel located in a first device unit adjacent to a second device unit that includes the target pixel. The corresponding pixel corresponds to the target pixel. The threshold region includes at least one pair of upper and lower limits. The target pixel is checked as a defective pixel when the raw datum is within the threshold region.

According to another embodiment of the present invention, an apparatus for detecting defects on a substrate comprises a support for supporting a substrate, a light source for irradiating a light on the substrate, an image detector for sensing a light reflected from the surface of the substrate, an analog-to-digital converter for converting the analog image information to a digital image information, a data process unit for calculating a raw datum of target pixel, a setting means for presetting a threshold region, and a judging means for judging whether or not the target pixel is a defective pixel. A plurality of device units are formed on a surface of the substrate, and each of the device units includes a plurality of pixels. The image detector forms analog image information on each of the pixels. The raw datum of a target pixel is formed by subtracting the image information of a corresponding pixel from the image information of the target pixel. The target pixel is a subject pixel for detecting defects. The corresponding pixel is a pixel located in a first device unit adjacent to a second device unit that includes the target pixel and corresponds to the target pixel. The threshold region includes at least one pair of upper and lower limits. The judging means compares the raw datum of the target pixel with the threshold region.

With the above exemplary embodiments, the killer defects can be detected separate from the non-killer defects.

BRIEF DESCRIPTION OF THE DRAWINGS

The above and other objects and advantages of the present invention will become readily apparent by reference to the following detailed description when considering in conjunction with the accompanying drawings, in which.

DESCRIPTION OF THE PREFERRED EMBODIMENTS

The present invention now will be described more fully hereinafter with reference to the accompanying drawings, in which exemplary embodiments of the present invention are shown.

Figure 7:
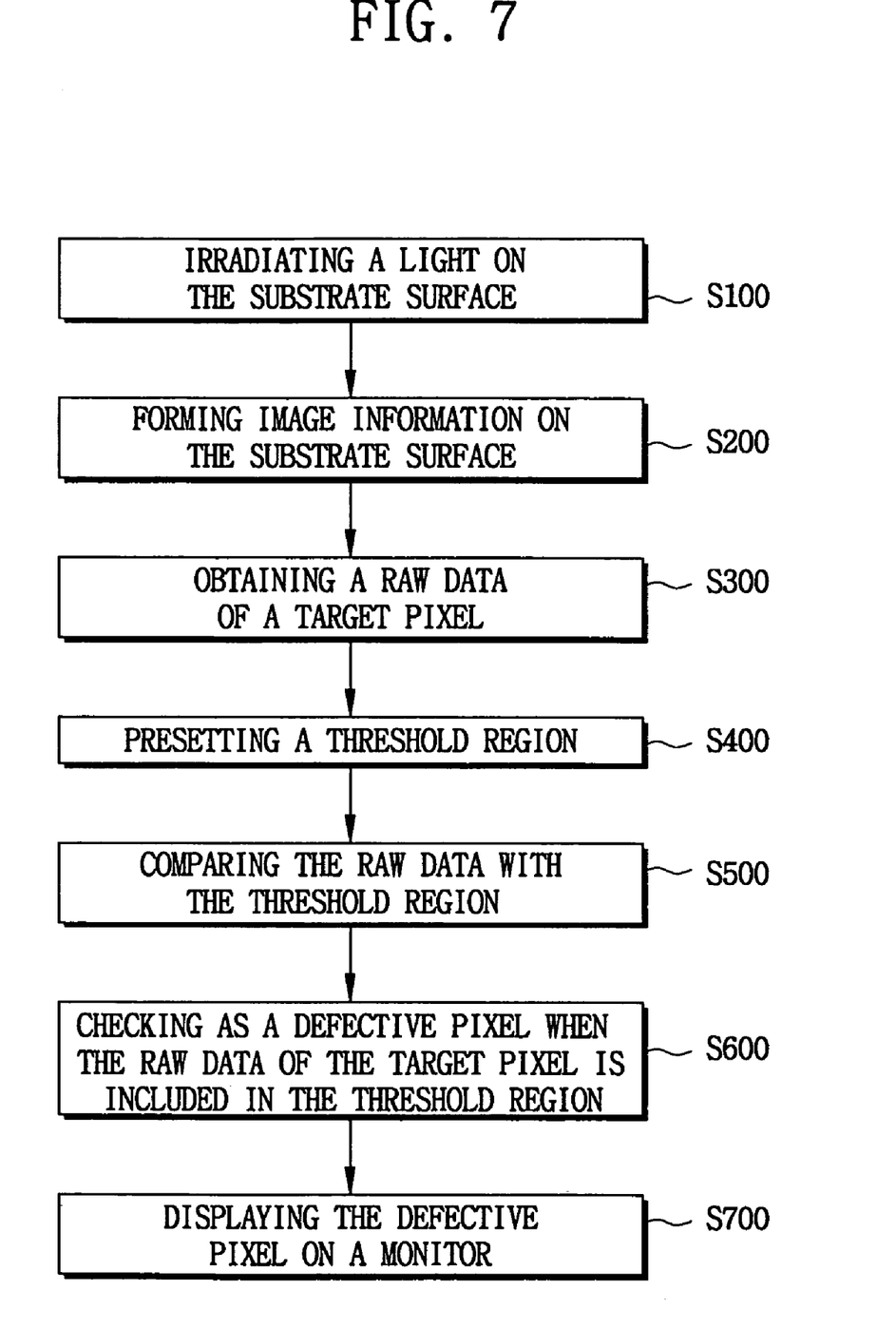
FIG. 7 is a flow chart illustrating a method of detecting a defection a substrate according to an embodiment of the present invention.

Referring to FIG. 7, a light is irradiated on a surface of the substrate on which a predetermined process has already been carried out so as to detect defects in step S100. A plurality of device units formed on the substrate surface have the same pattern, and each of the device units includes a plurality of pixels. As an exemplary embodiment, the substrate may be a wafer for fabricating a semiconductor device, and the device unit may be a unit cell operating as an independent electronic circuit on the wafer. In addition, the light may have a relatively short wavelength, which is referred to as a short-wave light. Therefore, the light is relatively well reflected, hardly diffracts and hardly interferes on the substrate surface. For example, an ultraviolet light may be irradiated on the substrate surface.

In the following step S20, image information on each pixel is formed by the device unit through sensing the light reflected from the substrate surface. As an exemplary embodiment, the reflected light may be received by a photosensor, and detected by a detecting unit. As a result, analog image information on each of the pixels is formed. The analogue image information is stored for every device unit. The analog image information may be converted into digital image information by using the ADC. As an exemplary embodiment, the digital image information may be expressed as a gray scale distinguishable by a relative density of black and white. The gray scale may be divided into 256 different levels by using an 8-bit microprocessor. Hereinafter, one of the 256 levels of the gray scale is referred to as a gray level.

Subsequently in step S300, a raw datum of a target pixel is obtained by subtracting the gray level of a corresponding pixel from the gray level of the target pixel. The target pixel is a subject pixel for detecting a defect. The corresponding pixel is a neighboring pixel positioned in a first device unit adjacent to a second device unit that includes the target pixel corresponding to the target pixel. Accordingly, when the wafer is normally processed, the corresponding pixel has the same pattern as that of the target pixel even though the corresponding pixel and the target pixel are positioned on different cells of the wafer from each other, and as a result, the gray level of the corresponding pixel should be identical to the gray level of the target pixel. Therefore, the discordance of the target pixel gray level with the corresponding pixel gray level indicates that the target pixel is a defective pixel. The gray level is expressed as a binary digit system, and thus the difference between the gray levels is obtained by subtraction of the binary digit indicating the gray level. According to the present embodiment of the invention, the difference of the gray levels itself is used as the criterion for detecting a defect regardless of subtraction result, i.e., positive or negative value of the difference. Accordingly, a defect corresponding to a positive raw datum can be prevented from being mistakenly detected together with a defect corresponding to a negative raw datum.

A threshold region, which is a criterion for judging defectiveness of a target pixel, is then preset in step S400, and the raw datum is compared with the threshold region in step S500. The threshold region is defined by an upper limit and a lower limit, each of which is a predetermined gray level difference. According to the conventional method of detecting defects as described above, the target pixel is checked as defective pixel when the raw datum is greater than the threshold region. In contrast, according to the present embodiment of the invention, the target pixel is checked as a defective pixel only when the raw datum is greater than the lower limit and smaller than the upper limit. Thus, when the raw datum is included in the threshold region, the target pixel is checked as a defective pixel. Finally, the defective pixel is displayed on a monitor for visual observation, and the defect type is visually verified.

Figure 8:
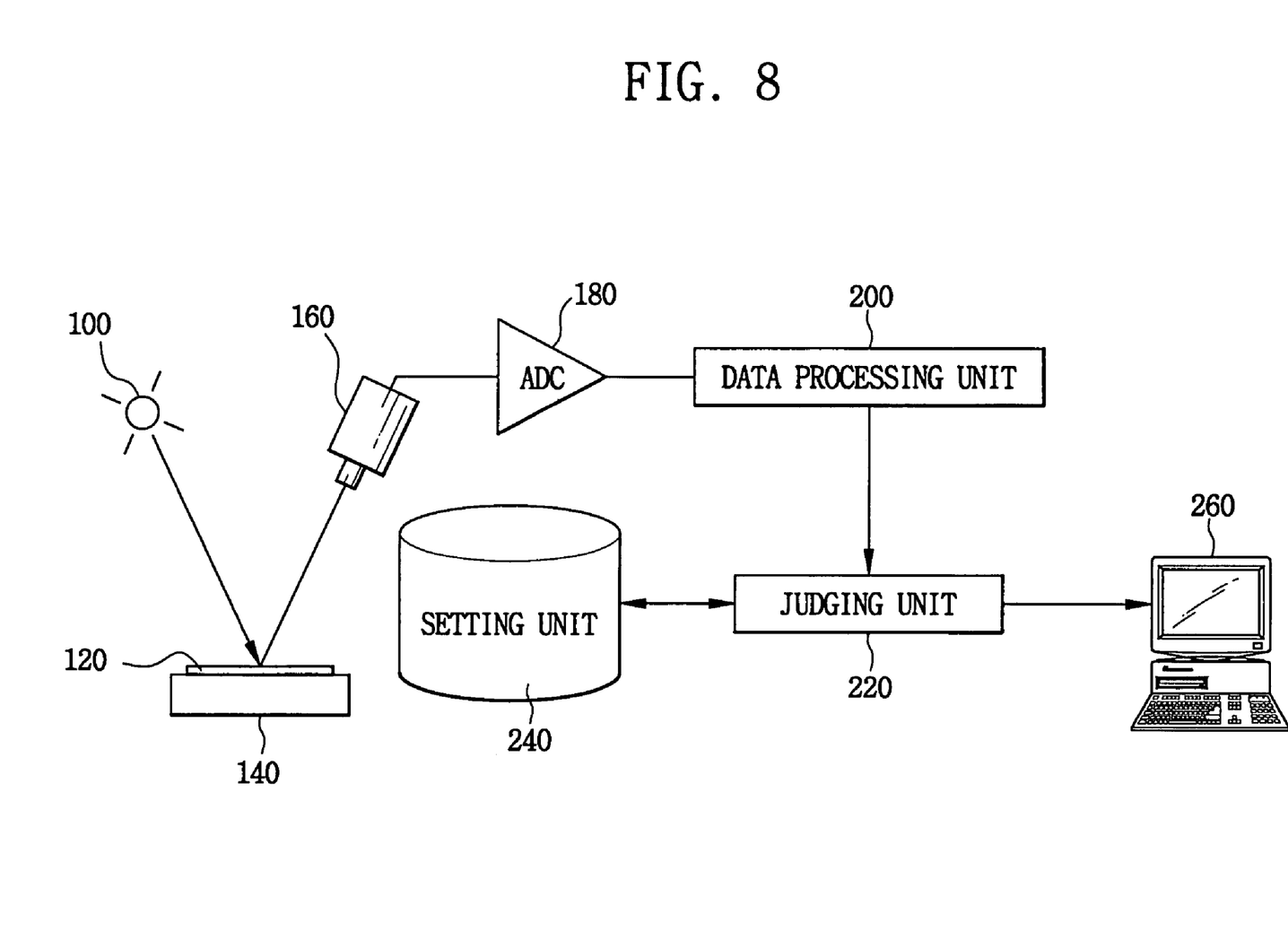
FIG. 8 is a schematic diagram showing an apparatus for detecting a defect according to another embodiment of the present invention.

Referring to FIG. 8, an apparatus for detecting a defect includes a support 140 for supporting a substrate on which a predetermined process has already been carried out. For example, the substrate may be a wafer for fabricating a semiconductor having undergone a chemical mechanical polishing (CMP) process, an etch-back process, a contact process, or an etching process.

A plurality of device units formed on the substrate surface have the same pattern, and each of the device units includes a plurality of pixels. When the substrate is a wafer for fabricating a semiconductor device, the device unit is a unit cell operating as an independent electronic circuit on the wafer. The conventional loading system such as a robot arm may be used for loading/unloading the wafer to/from the support. Hereinafter, the apparatus for detecting a defect according to the present invention is exemplarily described with regard to the wafer for fabricating a semiconductor device and the cell on the wafer. However, the present invention is not limited to the wafer for fabricating a semiconductor device, as would be known to one of the ordinary skill in the art.

A light is irradiated on a surface of the wafer 120 positioned on the support 140 from the light source 100, and reflected from the wafer surface. An image detector 160 including a photo-sensor detects the reflected light, and generates analog image information for every pixel on each device unit.

An analog-to-digital converter 180 transforms the analog image information into digital image information. As an exemplary embodiment, the digital image information may be expressed as a gray scale distinguishable by a relative density of black and white. The gray scale is divided into 256 different levels by using an 8-bit microprocessor, thus the pixel has a level among the 256 different levels, which is referred to as a gray level corresponding to the pixel. Accordingly, when the gray level is obtained for every pixel of a cell, all of the gray levels constitute the digital image information of the cell as a whole. When the digital image information of each cell on the wafer is obtained, an image map for a wafer is formed.

A data process unit 200 generates a raw datum of a target pixel by subtracting the gray level of a corresponding pixel from the gray level of the target pixel. The target pixel is a subject pixel for detecting a defect. The corresponding pixel is a neighboring pixel positioned in a first device unit adjacent to a second device unit that includes the target pixel corresponding to the target pixel.

A setting unit 240 presets a threshold region, which is a criterion for judging defectiveness of the target pixel. The threshold region is defined by an upper limit and a lower limit, each of which is a predetermined gray level difference.

A judging unit 220 compares the raw datum with the threshold region, and determines whether or not the target pixel is defective. The target pixel is checked as a defective pixel when the raw datum is greater than the lower limit and smaller than the upper limit. That is, when the raw datum is included in the threshold region, the target pixel is checked as a defective pixel. The judging unit 220 includes a central process unit (CPU) and a co-processor, which is an auxiliary processor for supporting the CPU during a numerical operation, and is operated by a main program and a plurality of sub-programs. Finally, the defective pixel is displayed on a monitor for visual observation, and the defect type is visually verified.

Figure 9:
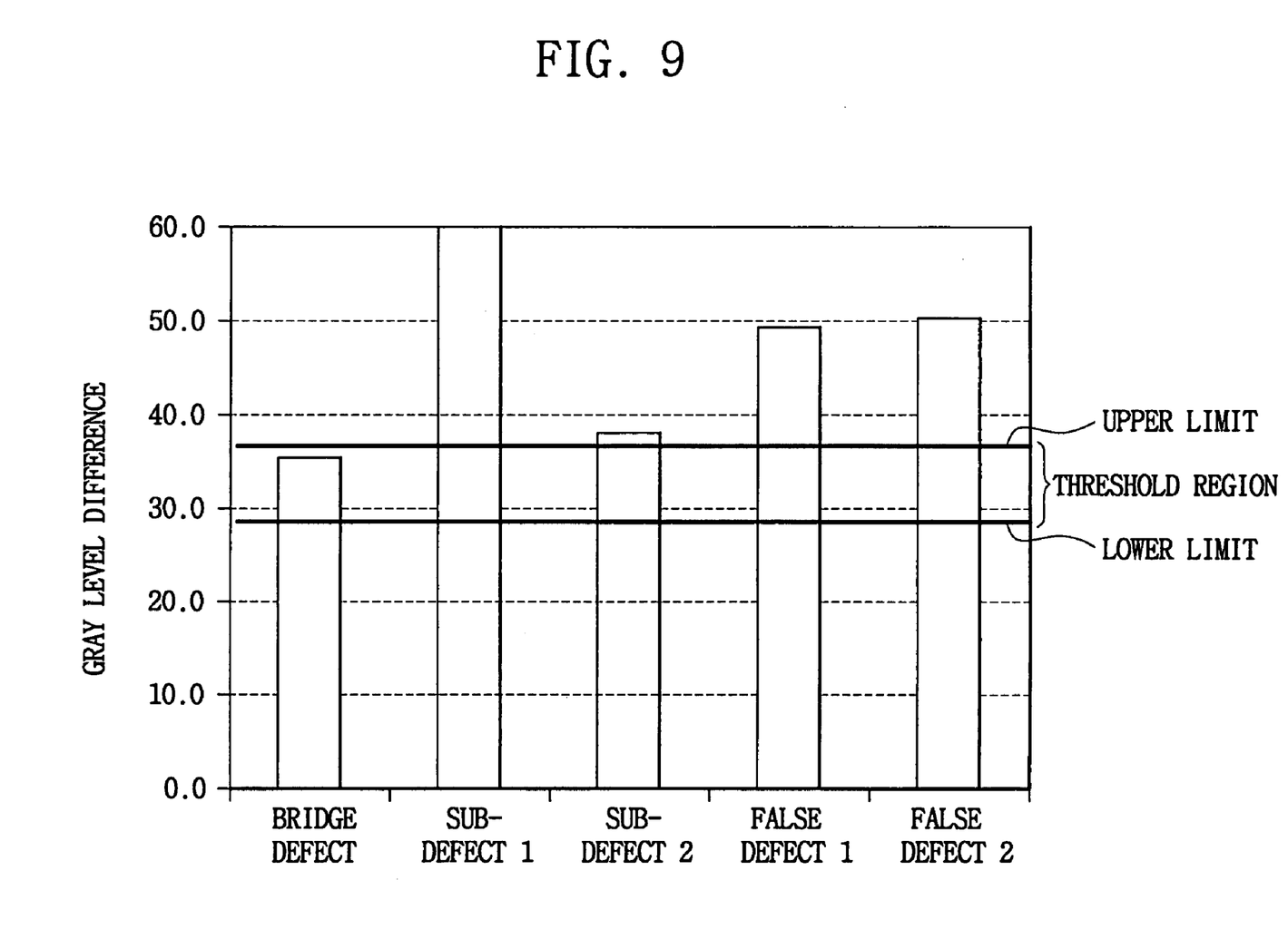
FIG. 9 is a graph illustrating a comparison between the threshold region according to an embodiment of the invention and the gray level difference according to the detected defect type.

FIG. 9 is a graph illustrating a comparison between the threshold region according to an embodiment of the invention and the gray level difference according to the detected defect type. The various defects shown in FIG. 9 are verified through the ADI process performed on a wafer including the NVM gate as shown in FIG. 5. The horizontal axis of the graph indicates the defect type, whereas the vertical axis of the graph indicates the gray level difference.

Referring to FIG. 9, as an exemplary embodiment, the threshold region for detecting the bridge defect, which is a killer defect generated during the NVM fabricating process, is defined by a lower limit that is identical to the conventional threshold value of 30 and by an upper limit above which a sub-defect and a false defect are detected. Accordingly, a sub-defect and the false defect are not detected since the gray level differences of a sub-defect and a false defect are more than the upper limit. As a result, the above defined threshold region can only detect the bridge defect separate from the sub-defect and the false defect. That is, proper selection of the upper limit makes it possible for the threshold region only to detect the killer defect separate from non-killer defects that are usually detected together with the killer defect. Therefore, the threshold region of the invention can improve the accuracy and promptness of defect detection, thereby improving the process efficiency.

Figure 10:
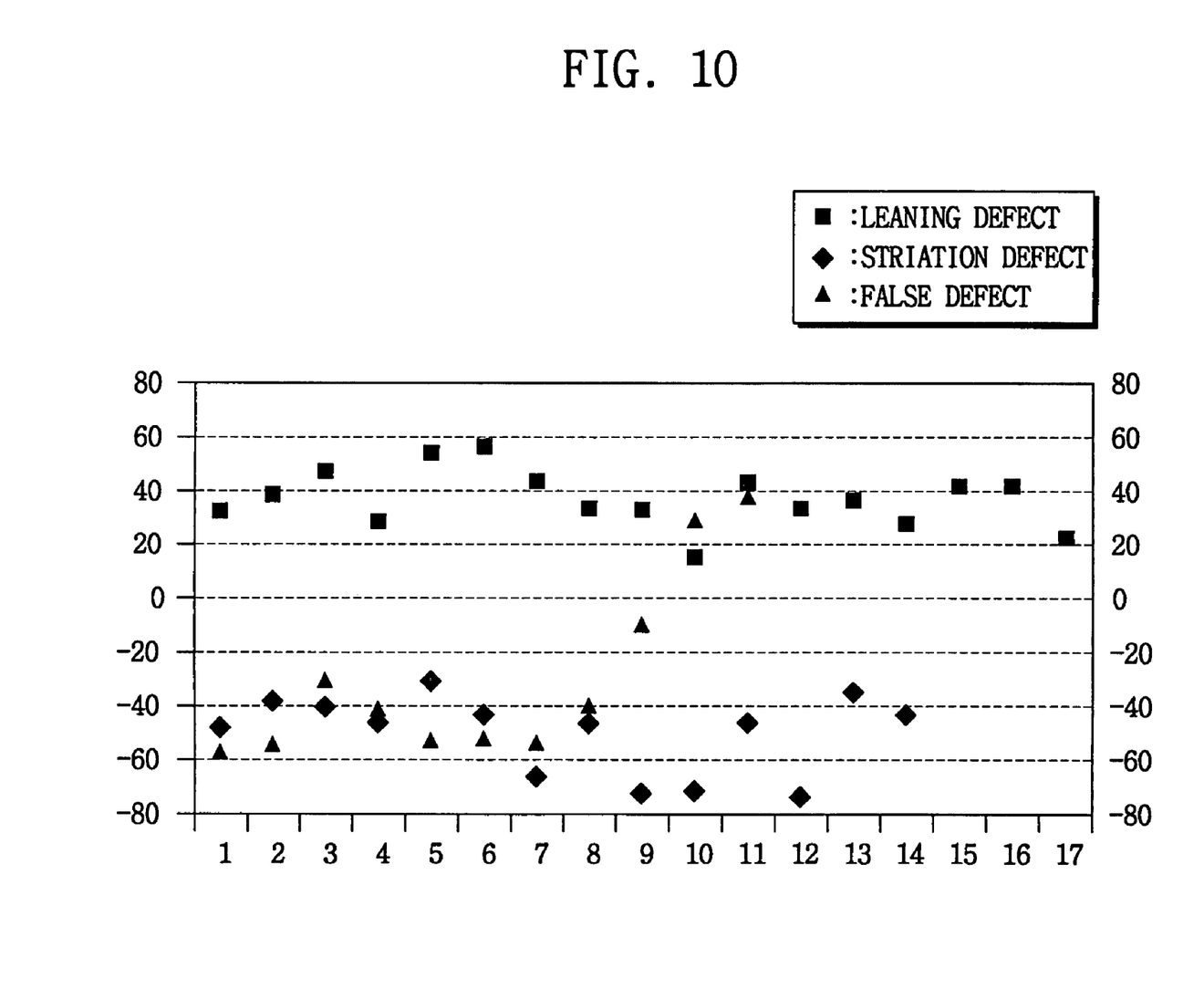
FIG. 10 is a graph illustrating the gray level difference with respect to the defect type occurring during the S-poly patterning process, according to yet another embodiment of the invention.

FIG. 10 is a graph showing the gray level difference with respect to the defect type that occurs during the S-poly patterning process. The horizontal axis of the graph indicates an arbitrary position on the surface of the wafer, and a vertical line of the graph indicates the gray level difference.

The graph illustrated in FIG. 10 shows that the leaning defect, a killer defect that occurs during the S-poly patterning process, is most frequently detected in a gray level difference range between about 20 and about 60, and the striation defect, a non-killer defect during the S-poly patterning process, is most frequently detected in a gray level difference range between about −20 and about −60. According to the conventional detecting method using the absolute value of the raw datum, the leaning defect is detected together with the striation defect. However, according to the invention of detecting method using the raw datum itself, the leaning defect is detected separate from the striation defect. Accordingly, the apparatus for detecting a defect has advantages in that the accuracy and promptness of defect detection is improved and the process efficiency is also enhanced.

According to the present invention, the raw datum of the target pixel is compared with the threshold region, and the target pixel is checked as a defective pixel when the raw datum is included in the threshold region. Therefore, the killer defect can more possibly be detected separate from the non-killer defects that are usually detected together with the killer defect. Thus, the accuracy and promptness of the defect detection is improved and the process efficiency is also enhanced.

Although the above exemplary embodiments discuss the method and apparatus for detecting a defect in the array mode, the method and apparatus disclosed could also be applicable in the random mode known to one of the ordinary skill in the art, since both of the array and the random mode are based on the comparison so as to detect a defect on the wafer.

Although the exemplary embodiments of the present invention have been described, it is understood that the present invention should not be limited to these exemplary embodiments but various changes and modifications can be made by one skilled in the art within the spirit and scope of the present invention as hereinafter claimed.

What is claimed is:

1. A method of detecting a defect on a substrate, the method comprising:
    irradiating a light on a substrate, wherein the substrate has a plurality of device units formed thereon with the same pattern, the plurality of device units each including a plurality of pixels;
    measuring image information for the plurality of pixels by sensing the light reflected by a surface of the substrate from the irradiating light;
    calculating a raw datum of a target pixel by subtracting the image information of a corresponding pixel from the image information of the target pixel, wherein the target pixel is a subject pixel for detecting a defect, and wherein the corresponding pixel is located in a first device unit that is adjacent to a second device unit that includes the target pixel, the corresponding pixel corresponding to the target pixel;
    presetting a threshold region including at least one pair of upper and lower limits;
    comparing the threshold region with the raw datum; and
    marking the target pixel as defective if the raw datum is within the threshold region.

2. The method of claim 1, wherein the substrate includes a wafer for fabricating a semiconductor device, and the plurality of device units are unit cells operating as independent electronic circuits on the wafer.

3. The method of detecting a defect on a substrate of claim 1, wherein the irradiating light includes a short-wave light.

4. The method of detecting a defect on a substrate of claim 3, wherein the short-wave light includes an ultraviolet light.

5. The method of detecting a defect on a substrate of claim 1, wherein the image information includes binary digital information.

6. The method of detecting a defect on a substrate of claim 5, wherein the image information represents a level on a gray scale, wherein the gray scale is distinguishable by a relative density of black and white.

7. The method of detecting a defect on a substrate of claim 6, wherein the gray scale is divided into 256 different levels.

8. The method of detecting a defect on a substrate of claim 1, further comprising displaying the defective pixel on a monitor.

9. An apparatus for detecting a defect on a substrate, the apparatus comprising:
  a support for supporting a substrate, wherein the substrate has a plurality of device units formed thereon, each device unit including a plurality of pixels;
  a light source for irradiating a light on the substrate;
  an image detector for sensing a reflecting light reflected by a surface of the substrate from the light source;
  a data processing unit for calculating a raw datum of a target pixel by subtracting digital image information of a corresponding pixel from digital image information of the target pixel, wherein the corresponding pixel is located in a first device unit that is adjacent to a second device unit that includes the target pixel, the corresponding pixel corresponding to the target pixel;
  a setting unit for presetting a threshold region, wherein the threshold region includes at least one pair of upper and lower limits; and
  a judging unit for judging whether or not the target pixel is a defective pixel by comparing the raw datum of the target pixel with the threshold region and marking the pixel as defective if within the threshold range.

10. The apparatus of claim 9, wherein the substrate is a wafer for fabricating a semiconductor device and the plurality of device units are unit cells operating as independent electronic circuits on the wafer.

11. The apparatus of claim 9, wherein the light in the light source includes a short-wave light.

12. The apparatus of claim 9, wherein the short-wave light includes an ultraviolet light.

13. The apparatus of claim 9, wherein the image information is expressed as a gray scale distinguishable by a relative density of black and white.

14. The apparatus of claim 9, further comprising a monitor for displaying a defective pixel and the raw datum of the defective pixel.

15. The apparatus of claim 9, wherein the image detector includes a photo-sensor.

16. The apparatus of claim 9, wherein the image detector generates the analog image information for each pixel of each device units.

17. The apparatus of claim 16, further comprising an analog-to-digital converter for converting the analog image information to the digital image information.

18. The apparatus of claim 9, wherein the plurality of device units each have the same pattern.

19. A method of detecting a defect on a substrate, the method comprising:
  irradiating a light on a substrate, wherein the substrate has a plurality of device units on a surface thereof, each device unit including a plurality of pixels;
  measuring image information for the plurality of pixels by sensing the light reflected by a surface of the substrate from the irradiating light;
  calculating a raw datum of a target pixel by subtracting the image information of a corresponding pixel from the image information of the target pixel, wherein the target pixel is a subject pixel for detecting a defect, wherein the corresponding pixel is a pixel located in a first device unit and corresponds to the target pixel, and wherein the first device unit is located adjacent to a second device unit that includes the target pixel;
  presetting a threshold region including at least one pair of upper and lower limits not including a zero value within the region; and
  comparing the raw datum with the threshold region.

20. The method of claim 19, further comprising marking the target pixel as defective if the raw datum is within the threshold region.

21. The method of claim 19, wherein the plurality of device units each have the same pattern.

22. The method of claim 19, wherein the irradiating light includes a short-wave light.

23. The method of claim 22, wherein the short-wave light includes an ultraviolet light.

24. The method of claim 19, wherein the image information includes binary digital information.

25. The method of claim 24, wherein the image information represents a level on a gray scale, wherein the gray scale is distinguishable by a relative density of black and white.

26. The method of claim 25, wherein the gray scale is divided into 256 different levels.

27. The method of claim 19, further comprising displaying a defective pixel on a monitor.

* * * * *

UNITED STATES PATENT AND TRADEMARK OFFICE
CERTIFICATE OF CORRECTION

| | |
|---|---|
| PATENT NO. | : 7,466,853 B2 |
| APPLICATION NO. | : 10/749670 |
| DATED | : December 16, 2008 |
| INVENTOR(S) | : Deok-Yong Kim et al. |

It is certified that error appears in the above-identified patent and that said Letters Patent is hereby corrected as shown below:

Column 5, line 23, the word "defection" should read -- defect on --.

Signed and Sealed this

Twenty-first Day of April, 2009

JOHN DOLL
*Acting Director of the United States Patent and Trademark Office*